(12) United States Patent
Velladurai et al.

(10) Patent No.: US 11,078,167 B2
(45) Date of Patent: Aug. 3, 2021

(54) PROCESS FOR THE PREPARATION OF DEFERASIROX

(71) Applicants: AUROBINDO PHARMA LIMITED, Hyderabad (IN); Hero Velladurai, Hyderabad (IN); Janardhana Rao Vascuri, Hyderabad (IN); Ravi Shankar Sathu, Hyderabad (IN); Sivakumaran Meenakshisunderam, Hyderabad (IN)

(72) Inventors: Hero Velladurai, Hyderabad (IN); Janardhana Rao Vascuri, Hyderabad (IN); Ravi Shankar Sathu, Hyderabad (IN); Sivakumaran Meenakshisunderam, Hyderabad (IN)

(73) Assignee: Aurobindo Pharma Ltd, Hyderabad (IN)

( * ) Notice: Subject to any disclaimer, the term of this patent is extended or adjusted under 35 U.S.C. 154(b) by 0 days.

(21) Appl. No.: 16/632,318

(22) PCT Filed: Jul. 2, 2018

(86) PCT No.: PCT/IB2018/054902
§ 371 (c)(1),
(2) Date: Jan. 17, 2020

(87) PCT Pub. No.: WO2019/016637
PCT Pub. Date: Jan. 24, 2019

(65) Prior Publication Data
US 2020/0207725 A1    Jul. 2, 2020

(30) Foreign Application Priority Data

Jul. 19, 2017   (IN) .............................. 201741025653

(51) Int. Cl.
*C07D 249/08*       (2006.01)
*C07D 265/22*       (2006.01)

(52) U.S. Cl.
CPC ......... *C07D 249/08* (2013.01); *C07D 265/22* (2013.01)

(58) Field of Classification Search
CPC ............................ C07D 249/08; C07D 265/22

USPC ........................................................ 544/92
See application file for complete search history.

(56) References Cited

FOREIGN PATENT DOCUMENTS

WO    WO-2011021218 A2 *  2/2011  .............. A61P 39/04

* cited by examiner

*Primary Examiner* — Kahsay Habte
(74) *Attorney, Agent, or Firm* — Jay R. Akhave

(57) ABSTRACT

The present invention provides an improved process for the preparation of Deferasirox of Formula-I substantially free from 'hydrazino impurity' by the condensation of 2-(2-hydroxyphenyl)-4H-1,3-benzoxazin-4-one of Formula-IV with 4-hydrazino benzoic acid of Formula-V in a polar solvent.

Formula - I

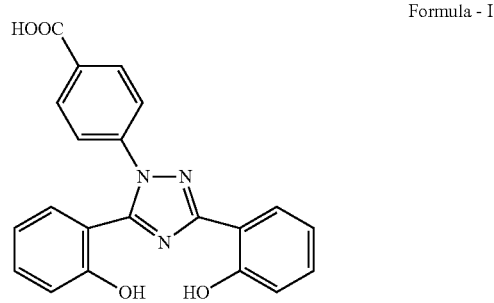

Formula - IV

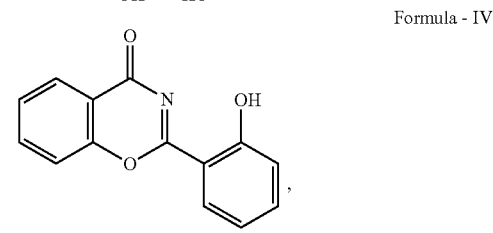

Formula - V

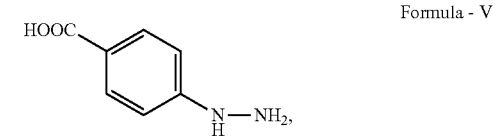

2 Claims, No Drawings

PROCESS FOR THE PREPARATION OF DEFERASIROX

FIELD OF THE INVENTION

The present invention relates to an improved process for the preparation of Deferasirox of Formula-I with high purity.

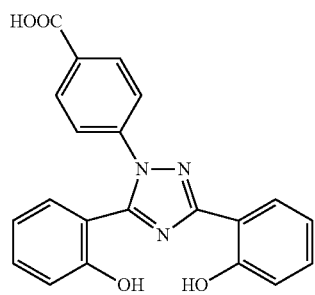

Formula - I

BACKGROUND OF THE INVENTION

Deferasirox of Formula-I is chemically known as 4-[3,5-bis(2-hydroxyphenyl)-1H-1,2,4-triazol-1-yl]benzoic acid. Deferasirox is approved by FDA and marketed as Exjade® in the form of Tablets for suspension & Jadenu® in the form of Tablets. It is a rationally designated iron chelator, which reduces chronic iron overload in patients receiving long-term blood transfusions for conditions such as β-thalassemia and other chronic anemia.

U.S. Pat. No. 6,465,504 discloses substituted 3,5-diphenyl-1,2,4-triazoles and their use as pharmaceutical metal chelators in which salicyloyl chloride of Formula-II is reacted with salicylamide of Formula-III at 170° C. to obtain slightly yellow color crystals of 2-(2-hydrophenyl)-4H-1,3-benzoxazin-4-one of Formula-IV having melting point 206-208° C., which is then reacted with 4-hydrazinobenzoic acid of Formula-V in the presence of ethanol under reflux conditions to obtain 4-[3,5-bis(2-hydroxyphenyl)-1H-1,2,4-triazol-1-yl]benzoic acid [Deferasirox] as colorless crystals having melting point 264-265° C.

The scheme for the preparation of Deferasirox is as depicted below:

Scheme-I

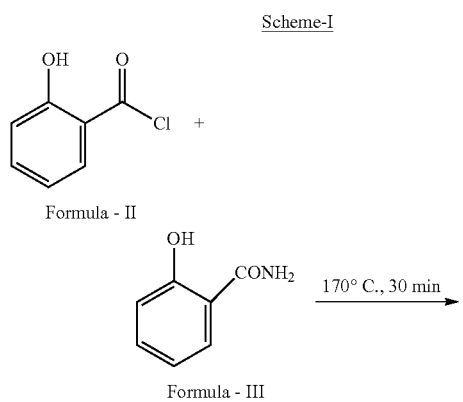

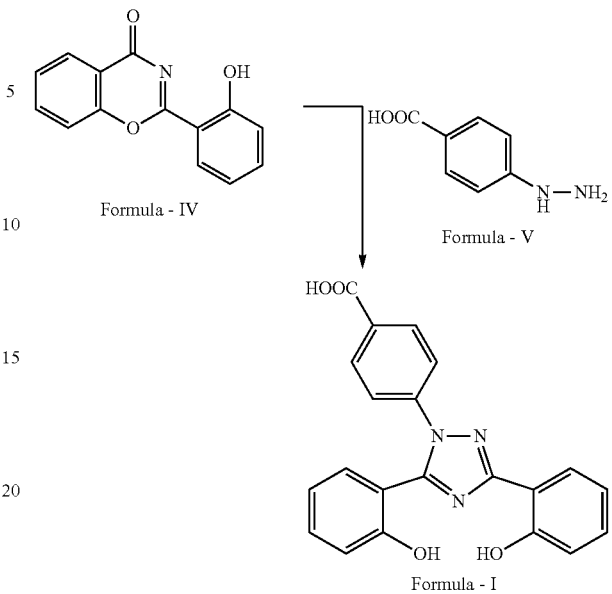

The reaction conditions employed for the preparation of Deferasirox results the material which does not meet the quality parameters such as chromatographic purity, and 4-hydrazinobenzoic acid content. In the reported procedure the condensation of salicyloyl chloride of Formula-II with salicylamide of Formula-III was conducted at 170° C., which is highly challenging and hazardous at commercial scales. This reaction at this combustible temperature generates by-products such as uncyclized derivatives, polymeric materials which are difficult to remove from the desired product. Further, in the reported procedure the condensation reaction of Formula-IV with 4-hydrazinobenzoic acid of Formula-V forms a heterogeneous reaction mass which results a small quantity of 4-hydrazinobenzoic acid as unreacted and retains in the final Deferasirox API as an impurity [hereinafter referred to as 'hydrazino impurity'], which has genotoxic, mutagenic and carcinogenic potential and is not easy to remove by conventional purification or crystallization techniques.

WO 03/053986 discloses a process for the preparation of Deferasirox of Formula-I comprises dissolving 4-hydrazinobenzoic acid of Formula-V in ethanol at reflux temperature and adding to this solution, 2-(2-hydrophenyl)-4H-1,3-benzoxazin-4-one of Formula-IV at reflux temperature.

The scheme for the preparation of Deferasirox is as depicted below:

Scheme-II

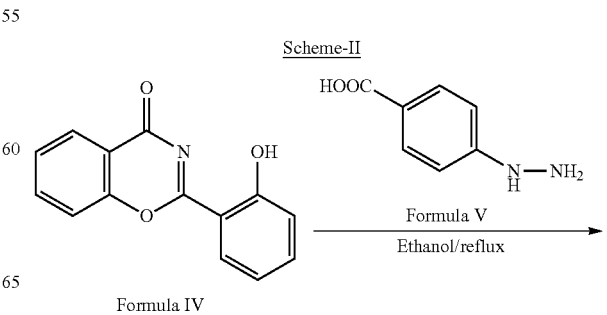

-continued

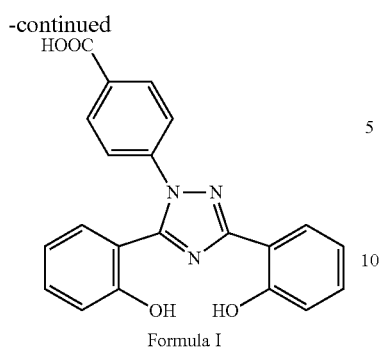

Formula I

Addition of the solid material of Formula IV at reflux temperature is not advisable at industrial scale.

WO09/094956 discloses a process for the preparation of Deferasirox which comprises the reaction of 4-hydrazinobenzoic acid of Formula-V with 2-(2-hydrophenyl)-4H-1,3-benzoxazin-4-one of Formula-IV in the presence of organic acid such as $C_1$-$C_4$ carboxylic acid.

The major drawback associated with the above mentioned processes is the incomplete reaction of 4-hydrazinobenzoic acid of Formula-V with 2-(2-hydrophenyl)-4H-1,3-benzoxazin-4-one of Formula-IV due to simultaneous precipitation of product during reaction and formation of heterogeneous reaction mass which results Deferasirox with hydrazino impurity having the range from 1000 ppm to 2000 ppm which is not easy to remove the impurity by conventional purification or crystallization methods.

Hence, there is a need of an improved process for the preparation of Deferasirox which not only devoid the disadvantage of the prior process as mentioned herein above but also gives high purity of Deferasirox. The process of the present invention overcomes the above disadvantages and gives high purity of Deferasirox.

OBJECTIVE OF THE INVENTION

The objective of the present invention is to provide an improved process for the preparation of Deferasirox of Formula-I which is industrially viable and gives Deferasirox with greater purity.

SUMMARY OF THE INVENTION

In an embodiment, the present invention provides Deferasirox which is substantially free of 'hydrazino impurity'.

In another embodiment, the present invention provides a process for the preparation of Deferasirox of Formula-I substantially free of 'hydrazino impurity', Formula - I which comprises:
(i) reacting 2-(2-hydrophenyl)-4H-1,3-benzoxazin-4-one of Formula-IV with 4-hydrazinobenzoic acid of Formula-V in a polar solvent to obtain Deferasirox of Formula-I;

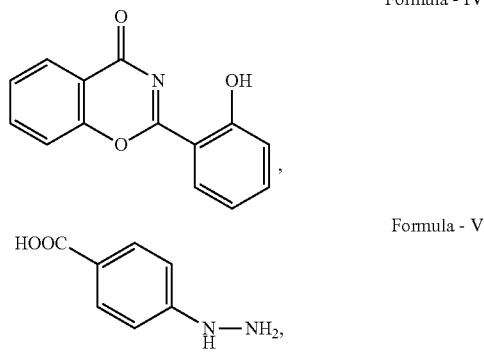

(ii) isolating Deferasirox of Formula-I.

The polar aprotic solvent used in step i) gives a homogeneous solution during the reaction and hence 4-hydrazinobenzoic acid of Formula-V reacts completely which results the pharmaceutically acceptable Deferasirox of Formula-I API substantially free of 'hydrazino impurity'.

In another embodiment, the present invention provides a process for the preparation of pure 2-(2-hydrophenyl)-4H-1,3-benzoxazin-4-one of Formula-IV,

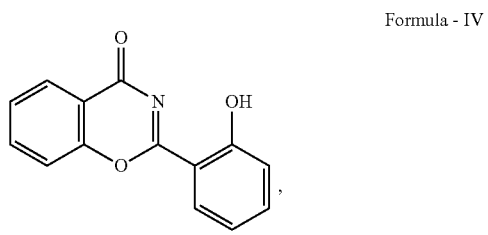 [SMILES: O=c1nc(-c2ccccc2O)oc2ccccc12]

which comprises:
(i) reacting Salicylic acid of Formula-VI with Salicylamide of Formula-III in the presence of a chlorinating agent,

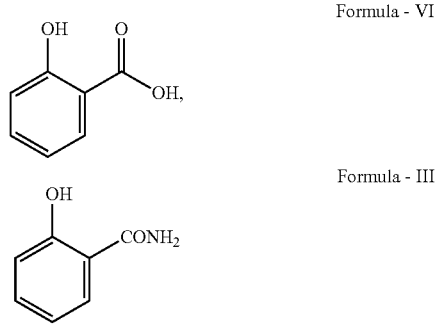

to obtain crude 2-(2-hydrophenyl)-4H-1,3-benzoxazin-4-one of Formula-IV;
(ii) treating the crude 2-(2-hydrophenyl)-4H-1,3-benzoxazin-4-one of Formula-IV with a base followed by treating with an acid to obtain pure 2-(2-hydrophenyl)-4H-1,3-benzoxazin-4-one of Formula-IV.

DETAILED DESCRIPTION OF THE INVENTION

In an embodiment, the present invention provides a process for the preparation of Deferasirox of Formula-I substantially free of 'hydrazino impurity',

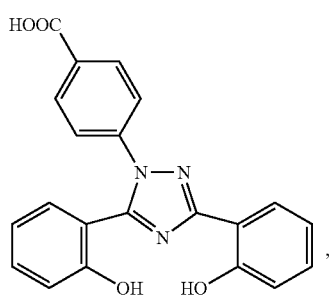

Formula - I which comprises:
(i) reacting 2-(2-hydrophenyl)-4H-1,3-benzoxazin-4-one of Formula-IV with 4-hydrazino benzoic acid of Formula-V in a polar solvent to obtain Deferasirox of Formula-I;

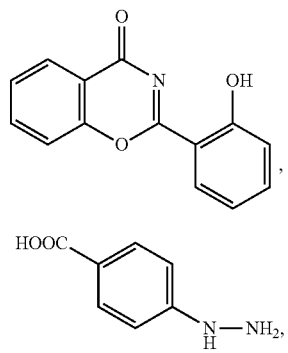

Formula - IV

Formula - V (ii) isolating Deferasirox of Formula-I.

step i) is conducted at reflux temperature.

The polar solvent used in step i) comprises tetrahydrofuran, N,N-dimethyl formamide, dimethyl sulfoxide, ethyl acetate, acetonitrile, $C_{1-4}$ alcohol or mixtures thereof.

As used herein "substantially free of hydrazino impurity" refers to Deferasirox has a purity of about 99% to about 99.99% and further comprising 'hydrazino impurity' in an amount of less than 20 ppm (parts per million). Specifically, Deferasirox as disclosed herein, contains less than about 2 ppm, more specifically less than about 0.5 ppm of 'hydrazino impurity', and most specifically is essentially free of 'hydrazino impurity'.

The content of 'hydrazino impurity' can be measured by the analytical techniques such High performance liquid chromatography [HPLC] and Liquid chromatography-mass spectrometry [LC-MS]. The content of hydrazino impurity is preferably measured by using the chromatographic technique HPLC [as per Pharmeuropa 29.2].

In another embodiment, the present invention provides a process for the preparation of pure 2-(2-hydrophenyl)-4H-1,3-benzoxazin-4-one of Formula-IV,

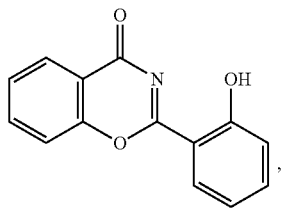

Formula - IV which comprises:
(i) reacting Salicylic acid of Formula-VI with Salicylamide of Formula-III in the presence of a chlorinating agent,

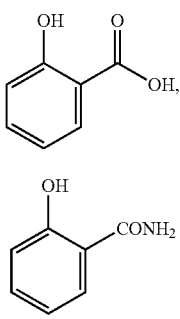

Formula - VI

Formula - III to obtain crude 2-(2-hydrophenyl)-4H-1,3-benzoxazin-4-one of Formula-IV;
(ii) treating the crude 2-(2-hydrophenyl)-4H-1,3-benzoxazin-4-one of Formula-IV with a base followed by treating with an acid to obtain pure 2-(2-hydrophenyl)-4H-1,3-benzoxazin-4-one of Formula-IV.

step i) is conducted at a temperature from 100° C. to 125° C.

Chlorinating agent used in step i) comprises thionyl chloride, oxalyl chloride, phosphorous pentachloride, phosphorous trichloride, phosphorous oxychloride methanesulfonyl chloride, trichloromethanesulfonyl chloride, tert-butyl hypochlorite, chloromethyl methyl ether, dichloromethyl methyl ether, methoxyacetyl chloride, Triphenylphosphine dichloride, cyanuric chloride, thrichloroisocyanuric acid, N-chloro succinimide, sodium dichloroisocyanurate, chloramine T dihydrate, dichloramine B, dichloramine T, benzyltrimethyl ammonium tetrachloroiodate and like.

The reaction of step i) performed in the presence of catalytic amounts of pyridine and aluminium chloride and a solvent comprises o-xylene, toluene, tetrahydrofuran, hexane, diethyl ether, 1,4-dioxane or mixtures thereof.

Base used in step ii) comprises organic base selected from but not restricted to lithium methoxide, sodium methoxide, potassium methoxide; tetrabutylammonium methoxide, lithium isopropoxide, triethyl amine, diisopropyl methyl amine, methyl amine, dimethyl amine or mixtures thereof and inorganic base selected from but not restricted to alkaline or alkaline earth metal hydroxide, alkaline or alkaline earth metal carbonate or mixtures thereof.

Acid used in step ii) comprises organic acid selected from but not restricted to formic acid, acetic acid, oxalic acid, propanoic acid, lactic acid, maleic acid, citric acid, valeric acid, benzoic acid or mixtures thereof and inorganic acid selected from but not restricted to hydrochloric acid, sulphuric acid, phosphoric acid, nitric acid, or mixtures thereof.

The following example(s) illustrate the nature of the invention and are provided for illustrative purposes only and should not be construed to limit the scope of the invention.

Example 1

Preparation of 4-[3,5-Bis(2-hydroxyphenyl)-1H-1,2,4-triazol-1-yl]benzoic Acid (Deferasirox)

10 grams of 2-(2-Hydroxyphenyl)-4H-1,3-benzoxazin-4-one (Deferasirox cyclic compound) and 6.5 grams of 4-hydrazinobenzoic acid were boiled under reflux temperature for 2 hours in 70 ml absolute alcohol. The product was precipitated during reflux and cooled to room temperature, filtered and washed with absolute alcohol (2×10 ml). The obtained wet Deferasirox (16 grams) was dissolved in absolute alcohol (430 ml) at reflux temperature, charcolized, filtered through hyflo bed at hot condition and then washed with hot absolute alcohol (20 ml). Filtrate was distilled off until the mass volume reaches about 100 ml and cooled to room temperature. The precipitated product was filtered and washed with absolute alcohol. The product was dried at 50-55° C. for 6 hours, obtained about 13 grams of pure 4-[3,5-Bis(2-hydroxyphenyl)-1H-1,2,4-triazol-1-yl]benzoic acid [HPLC Purity: 99.95%; 'hydrazino impurity': 110 ppm].

Example 2

Preparation of 4-[3,5-Bis(2-hydroxyphenyl)-1H-1,2,4-triazol-1-yl]benzoic Acid (Deferasirox)

10 grams of 2-(2-Hydroxyphenyl)-4H-1,3-benzoxazin-4-one and 6.5 grams of 4-hydrazinobenzoic acid were boiled under reflux temperature for 10 hours in 100 ml tetrahydrofuran (THF). Further reaction mass was cooled to room temperature and 100 ml absolute alcohol was added, reaction mass was filtered and washed with absolute alcohol (2×10 ml). The obtained wet Deferasirox (15.5 grams) was dissolved in absolute alcohol (430 ml) at reflux temperature, charcolized, filtered through hyflo bed at hot condition and washed with hot absolute alcohol (20 ml). Filtrate was distilled off until the mass volume reaches about 100 ml and cooled to room temperature. The precipitated product was filtered and washed with absolute alcohol. The product was dried at 50-55° C. for 6 hours, obtained about 9.8 grams of pure 4-[3,5-Bis(2-hydroxyphenyl)-1H-1,2,4-triazol-1-yl]benzoic acid [HPLC Purity: 99.98%; 'hydrazino impurity': 0.40 ppm].

Example 3

Preparation of 4-[3,5-Bis(2-hydroxyphenyl)-1H-1,2,4-triazol-1-yl]benzoic Acid (Deferasirox)

10 grams of 2-(2-Hydroxyphenyl)-4H-1,3-benzoxazin-4-one and 5.71 grams of 4-hydrazinobenzoic acid were boiled under reflux temperature for 9 hours in 120 ml tetrahydrofuran (THF). Reaction mass was distilled and 100 ml absolute alcohol was added and co-distilled until the mass volume reaches to about 70 ml and cooled to room temperature, filtered and washed with absolute alcohol (2×10 ml). The obtained wet Deferasirox (17 grams) was dissolved in absolute alcohol (430 ml) at reflux temperature, charcolized, filtered through hyflo bed at hot condition and washed with hot absolute alcohol (20 ml). Filtrate was distilled off until the mass volume reaches about 100 ml and cooled to room temperature. The precipitated product was filtered and washed with absolute alcohol. The product was dried at 50-55° C. for 6 hours, obtained about 10.2 grams of pure 4-[3,5-Bis(2-hydroxyphenyl)-1H-1,2,4-triazol-1-yl]benzoic acid [HPLC Purity: 99.98%; 'hydrazino impurity': 0.15 ppm].

Example 4

Preparation of 4-[3,5-Bis(2-hydroxyphenyl)-1H-1,2,4-triazol-1-yl]benzoic Acid (Deferasirox)

10 grams of 2-(2-Hydroxyphenyl)-4H-1,3-benzoxazin-4-one and 6.05 grams of 4-hydrazinobenzoic acid were boiled under reflux temperature for 9 hours in 150 ml tetrahydrofuran (THF). Reaction mass distilled and added 150 ml absolute alcohol and co-distilled until the mass volume reaches about 70 ml and cooled to room temperature, filtered and washed with absolute alcohol (2×10 ml). The obtained wet Deferasirox (17 grams) was dissolved in absolute alcohol (430 ml) at reflux temperature, charcolized, filtered through hyflo bed at hot condition and washed with hot absolute alcohol (20 ml). Filtrate was distilled off until the mass volume reaches about 100 ml and cooled to room temperature. The precipitated product was filtered and washed with absolute alcohol. The product was dried at 50-55° C. for 6 hours, obtained about 11.6 grams of pure 4-[3,5-Bis(2-hydroxyphenyl)-1H-1,2,4-triazol-1-yl]benzoic acid [HPLC Purity: 99.98%; 'hydrazino impurity': 0.21 ppm].

Example 5

Preparation of 4-[3,5-Bis(2-hydroxyphenyl)-1H-1,2,4-triazol-1-yl]benzoic Acid (Deferasirox)

10 grams of 2-(2-Hydroxyphenyl)-4H-1,3-benzoxazin-4-one and 6.35 grams of 4-hydrazinobenzoic acid were boiled under reflux temperature for 9 hours in 150 ml tetrahydrofuran (THF). Reaction mass distilled and added 150 ml absolute alcohol and co-distilled until the mass volume reaches about 70 ml and cooled to room temperature, filtered and washed with absolute alcohol (2×10 ml). The obtained wet Deferasirox (18 grams) was dissolved in absolute alcohol (430 ml) at reflux temperature, charcolized, filtered through hyflo bed at hot condition and washed with hot absolute alcohol (20 ml). Filtrate was distilled off until the mass volume reaches about 100 ml and cooled to room temperature. The precipitated product was filtered and washed with absolute alcohol. The product was dried at 50-55° C. for 6 hours, obtained about 12.6 grams of pure 4-[3,5-Bis(2-hydroxyphenyl)-1H-1,2,4-triazol-1-yl]benzoic acid [HPLC Purity: 99.98%; 'hydrazino impurity': 0.27 ppm].

Example 6

Preparation of 4-[3,5-Bis(2-hydroxyphenyl)-1H-1,2,4-triazol-1-yl]benzoic Acid (Deferasirox)

10 grams of 2-(2-Hydroxyphenyl)-4H-1,3-benzoxazin-4-one and 7.0 grams of 4-hydrazinobenzoic acid were boiled under reflux temperature for 9 hours in 150 ml tetrahydrofuran (THF). Reaction mass was distilled and 150 ml of absolute alcohol was added and co-distilled until the mass volume reaches up to 70 ml and cooled to room temperature, filtered and washed with absolute alcohol (2×10 ml). The obtained wet Deferasirox (18 grams) was dissolved in absolute alcohol (430 ml) at reflux temperature, charcolized, filtered through hyflo bed at hot condition and washed with hot absolute alcohol (20 ml). Filtrate was distilled off until the mass volume reaches about 100 ml and cooled to room temperature. The precipitated product was filtered and washed with absolute alcohol. The product was dried at 50-55° C. for 6 hours, obtained about 12.3 grams of pure 4-[3,5-Bis(2-hydroxyphenyl)-1H-1,2,4-triazol-1-yl]benzoic acid [HPLC Purity: 99.98%; 'hydrazino impurity': 0.48 ppm].

Example 7

Preparation of 4-[3,5-Bis(2-hydroxyphenyl)-1H-1,2,4-triazol-1-yl]benzoic Acid (Deferasirox)

10 grams of 2-(2-Hydroxyphenyl)-4H-1,3-benzoxazin-4-one and 6.65 grams of 4-hydrazinobenzoic acid were boiled under reflux temperature for 9 hours in 150 ml tetrahydrofuran (THF). Reaction mass distilled and added 150 ml absolute alcohol and co-distilled until the mass volume reaches about 80 ml and cooled to room temperature, filtered and washed with absolute alcohol (2×10 ml). The obtained wet Deferasirox (16.5 grams) was dissolved in absolute alcohol (430 ml) at reflux temperature, charcolized, filtered through hyflo bed at hot condition and washed with hot absolute alcohol (20 ml). Filtrate was distilled off until the mass volume reaches about 100 ml and cooled to room temperature. The precipitated product was filtered and washed with absolute alcohol. The product was dried at 50-55° C. for 6 hours, obtained about 12.2 grams of pure 4-[3,5-Bis(2-hydroxyphenyl)-1H-1,2,4-triazol-1-yl]benzoic acid [HPLC Purity: 99.98%; 'hydrazino impurity': 0.39 ppm].

Example 8

Preparation of 2-(2-Hydroxyphenyl)-4H-1,3-Benzoxazin-4-one (Deferasirox Cyclic Compound)

10 grams of salicylamide, 10.90 grams of salicylic acid, 0.20 grams aluminum chloride and 1.17 grams pyridine were added to 55 ml o-xylene at 25-30° C. Reaction mass temperature was raised to 115-125° C. and then 16.70 grams thionyl chloride was slowly added over a period of 60 min at 115-125° C. and maintained at 115-125° C. for 30 min. The reaction mass was cooled to 25-30° C. and further added 33 ml absolute alcohol. The obtained slurry product was filtered and washed with absolute alcohol to give 15 grams of pale yellow crystalline 2-(2-hydroxyphenyl)-4H-1,3-benzoxazin-4-one having chromatographic purity about 95.5%.

The above product was purified by refluxing in absolute alcohol in presence of sodium methoxide followed by glacial acetic acid addition and then cooled to room temperature. The product was filtered and washed with absolute alcohol to obtain pure 2-(2-hydroxyphenyl)-4H-1,3-benzoxazin-4-one having chromatographic purity about 99.5%.

We claim:
1. A process for the preparation of Deferasirox of Formula (I):

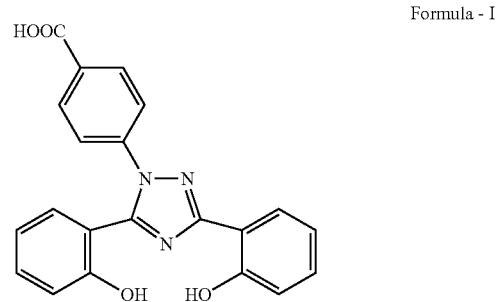 [SMILES: O=C(O)c1ccc(-n2nc(-c3ccccc3O)nc2-c2ccccc2O)cc1]

Formula - I which comprises:
(i) reacting 2-(2-hydrophenyl)-4H-1,3-benzoxazin-4-one of Formula-IV with 4-hydrazinobenzoic acid of Formula-V in a polar solvent selected from the group comprising tetrahydrofuran, N,N-dimethyl formamide, Dimethyl sulfoxide, acetonitrile, or mixtures thereof to obtain Deferasirox of Formula-I

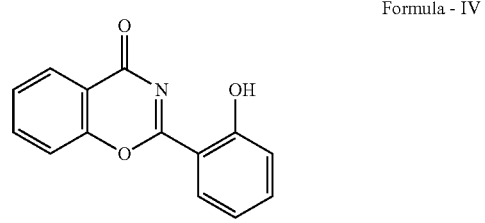

Formula - IV

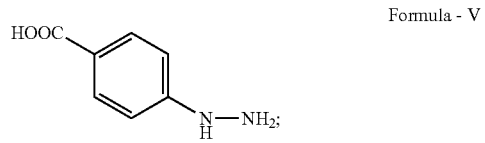

Formula - V (ii) isolating Deferasirox of Formula-I.
2. The process according to claim 1 Deferasirox contains less than about 0.5 ppm of 'hydrazino impurity'.

* * * * *